United States Patent [19]
Pander et al.

[11] Patent Number: 5,254,711
[45] Date of Patent: Oct. 19, 1993

[54] CONTINUOUS PREPARATION OF 3-CYANO-3,5,5-TRIMETHYLCYCLOHEXANONE

[75] Inventors: Hans J. Pander, Roedersheim-Gronau; Hardo Siegel, Speyer; Otto Woerz, Friedelsheim, all of Fed. Rep. of Germany

[73] Assignee: BASF Aktiengesellschaft, Ludwigshafen, Fed. Rep. of Germany

[21] Appl. No.: 14,171

[22] Filed: Feb. 5, 1993

[30] Foreign Application Priority Data

Feb. 7, 1992 [DE] Fed. Rep. of Germany ....... 4203456

[51] Int. Cl.⁵ .......................................... C07C 253/30
[52] U.S. Cl. .................................................. 558/341
[58] Field of Search ........................................ 558/341

[56] References Cited

U.S. PATENT DOCUMENTS

| | | | |
|---|---|---|---|
| 3,270,044 | 8/1966 | Schmitt et al. | 558/341 |
| 4,299,775 | 11/1981 | Dubreux | 558/341 |
| 5,011,968 | 4/1991 | Thunberg et al. | 558/341 |
| 5,091,554 | 2/1992 | Huthmacher et al. | 558/341 |
| 5,142,090 | 8/1992 | Pontoglio et al. | 558/341 |
| 5,179,221 | 1/1993 | Tarahoso et al. | 558/341 |
| 5,183,915 | 2/1993 | Forguy et al. | 558/341 |

FOREIGN PATENT DOCUMENTS

| | | |
|---|---|---|
| 1085871 | 7/1960 | Fed. Rep. of Germany . |
| 1240521 | 5/1967 | Fed. Rep. of Germany . |
| 1240854 | 5/1967 | Fed. Rep. of Germany . |
| 887413 | 8/1962 | United Kingdom . |
| 1047920 | 11/1966 | United Kingdom . |

*Primary Examiner*—Joseph Paul Brust
*Attorney, Agent, or Firm*—Keil & Weinkauf

[57] ABSTRACT

Abstract of the disclosure: A process for the continuous preparation of 3-cyano-3,5,5-trimethylcyclohexanone by base-catalyzed reaction of isophorone and hydrogen cyanide, comprises carrying out the reaction in two separate reaction zones
a) with essentially complete back-mixing and subsequently
b) essentially without back-mixing.

3 Claims, 1 Drawing Sheet

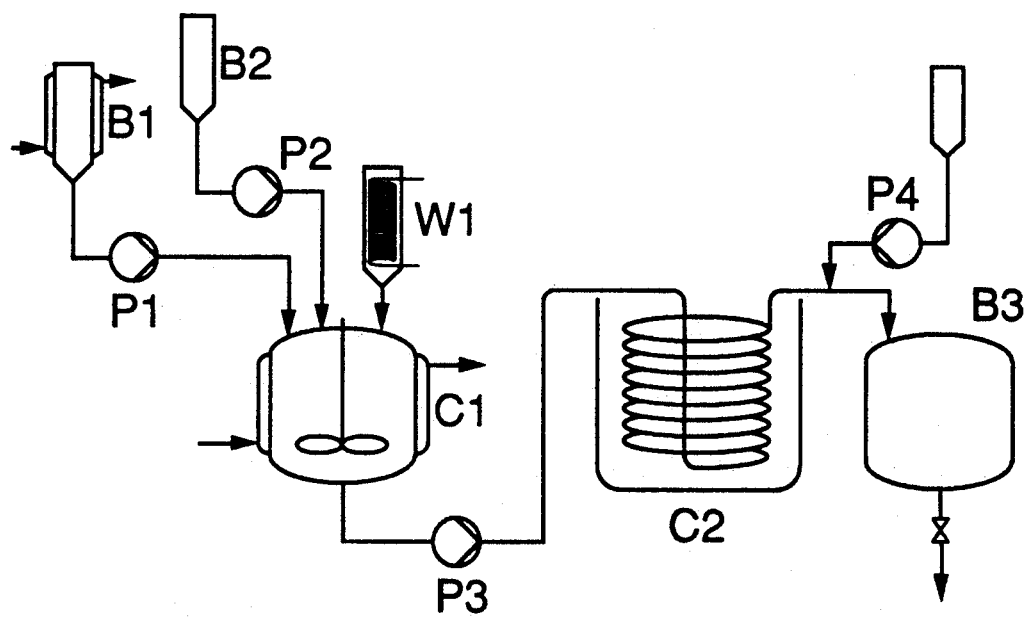

CONTINUOUS PREPARATION OF 3-CYANO-3,5,5-TRIMETHYLCYCLOHEXANONE

The present invention relates to a process for the continuous preparation of 3-cyano-3,5,5-trimethylcyclohexanone by base-catalyzed reaction of isophorone and hydrogen cyanide in two separate reaction zones.

It is known that 3-cyano-3,5,S-trimethylcyclohexanone can be prepared by reacting isophorone with hydrogen cyanide in the presence of highly alkaline catalysts. DE-A-10 85 871 discloses a process in which $\alpha,\beta$-unsaturated ketones and hydrogen cyanide are reacted in the presence of a highly alkaline catalyst and in the presence of a polar solvent to give the corresponding cyanoketones. The reaction is preferably carried out batchwise. In the reaction given as an example of isophorone and hydrogen cyanide in dimethylacetamide as solvent in the presence of 1.15% of potassium carbonate, 3-cyano-3,5,5-trimethylcyclohexanone is obtained in a yield of 70%.

DE-A-12 40 854 discloses a process in which 3-cyano-3,5,5-trimethylcyclohexanone yields of 96% are achieved in the absence of a solvent at catalyst concentrations of from $10^{-1}$ to $10^{-3}\%$ by weight, based on the reaction mixture. One of the examples described is a continuous process for the preparation of 3-cyano-3,5,5-trimethylcyclohexanone from isophorone and hydrogen cyanide in three successive stirred reactors. The mean residence time is 4 hours in the first reactor and one hour in each of the two subsequent reactors.

DE-A-12 40 521 describes a process in which the reaction of isophorone or mesityl oxide with hydrogen cyanide is carried out in the presence of alkaline catalysts supported on solid carrier materials. In order to achieve good yields of 3-cyano-3,5,5, -trimethylcyclohexanone, the proportion of HCN in the reaction mixture must be kept low.

The conversion of HCN is, for example, from 94 to 98%, corresponding to HCN concentrations in the fully reacted reaction mixture of from 0.1 to 0.4%. These relatively high HCN concentrations require a separate purification step if the process is utilized industrially.

It is an object of the present invention to overcome the abovementioned disadvantages.

We have found that this object is achieved by a novel and improved process for the continuous preparation of 3-cyano-3,5,5-trimethylcyclohexanone by base-catalyzed reaction of isophorone and hydrogen cyanide, which comprises carrying out the reaction in two separate reaction zones a) with essentially complete back-mixing and subsequently b) essentially without back-mixing.

The novel process can be carried out as follows:

The continuous base-catalyzed reaction of isophorone and hydrogen cyanide to give 3-cyano-3,5,5-trimethylcyclohexanone in two separate reaction zones a) and b) can be carried out at from 60° to 250° C., preferably from 100° to 210° C., particularly preferably from 130° to 180° C., and at from 0.01 to 5 bar, preferably from 0.1 to 2 bar, particularly preferably at atmospheric pressure. The isophorone:hydrogen cyanide molar ratio used is advantageously from 1.1:1 to 6:1, preferably from 1.3:1 to 2.5:1. The reaction can be carried out in the presence of an inert solvent, but is preferably carried out in the absence of an inert solvent.

a) The reactor having essentially complete back-mixing may be, for example, a stirred reactor, a mixing cycle or a loop reactor. The heat of reaction that is liberated is dissipated by means of suitable heat exchangers.

b) Suitable subsequent reactors are cylindrical reactors containing packing elements or fixed internals which fully or partially prevent back-mixing. However, when the synthesis is carried out on a laboratory scale it is also possible to employ a tubular reactor operated with turbulent flow.

Suitable basic catalysts are all substances which form cyanide ions in the presence of hydrogen cyanide under the reaction conditions. These include, for example, hydroxides, cyanides and alkoxides of the alkali and alkaline earth metals, and quaternary ammonium compounds. Preference is given to alkali metal $C_1$–$C_4$-alkoxides, such as sodium methoxide, sodium ethoxide, potassium methoxide, potassium tert-butoxide, and lithium methoxide, and particular preference is given to sodium methoxide.

The catalyst concentration is from 0.01 to 3% by weight, based on the reaction mixture. The catalyst concentration is preferably selected so that the solubility of the basic catalyst, which depends on the reaction temperature and the composition of the reaction mixture, is not exceeded; the concentrations are preferably from 0.01 to 0.3% by weight, based on the reaction mixture.

Examples of suitable inert solvents are dimethylformamide, dimethylacetamide, and N-methylpyrrolidone. However, the reaction is preferably carried out without addition of solvent.

The residence time necessary for complete conversion of the HCN depends on the reaction temperature and the catalyst concentration. It is generally from 1 to 4 hours for the stirred reactor and from 0.2 to 1.5 hours for the subsequent reactor operated without back-mixing.

The resultant reaction mixture can be extracted with water in order to remove the dissolved catalyst. However, the basic catalyst can also be neutralized by adding an equivalent amount or an excess of an organic or inorganic acid. After washing or stabilization by addition of an acid, the reaction mixture can be purified by fractional distillation. Unreacted isophorone can be recycled into the continuous reaction process.

This reactor combination offers considerable economic and safety advantages over a multistep condenser reactor cascade when the synthesis is carried out industrially.

The fact that the synthesis of isophorone nitrile from isophorone and hydrogen cyanide in this reaction combination would cause no problems was surprising. Rather, the high vapor pressure of hydrogen cyanide (boiling point 26° C.) gave rise to expectations that hydrogen cyanide gas would be released in the subsequent reactor when the process was carried out at atmospheric pressure.

3-cyano-3,5,5-trimethylcyclohexanone is an important intermediate in the synthesis of 5-amino-1-(aminomethyl)-1,3,3-trimethylcyclohexane (isophoronediamine) and the corresponding diisocyanate (EP-A-394 967 and EP-A-042 119).

EXAMPLES

The attached figure illustrates the examples below:

EXAMPLE 1

The continuous synthesis is carried out using a stirred flask having a capacity of 80 ml (C1) and a downstream tubular reactor with a length of 6 m and an internal diameter of 4 mm (C2) (see flow chart). The two reactors are thermostatically heatable. The stirred flask is vented via the brine-coolable condenser (W1).

A homogeneous solution of 62.95 g of isophorone and 6.15 g of anhydrous hydrogen cyanide stabilized with 50 ppm of phosphoric acid is metered hourly into the stirred reactor C1 by means of the pump P1 from the cooled tank B1, and 0.507 g of a 15% strength methanolic solution of sodium methoxide is metered into C1 by means of the micrometering pump P2 from tank B2. The reaction mixture continuously leaving the stirred reactor C1 is fed to the tubular reactor C2 by means of the pump B3. Separate heating circuits maintain a temperature of 150° C. in both reactors. The hydrogen cyanide content at the outlet to A. tubular reactor C2 is <50 ppm, corresponding to an HCN conversion of greater than 99.9%.

0.17 g/h of 85% strength phosphoric acid is added to the reaction mixture by means of the micrometering pump P4, and the mixture is collected in tank B3.

826 g of the stabilized reaction mixture are subjected to fractional distillation. After removal of 5.1 g of low-boiling components (methanol H$_2$O), 383.8 g of unreacted isophorone having a boiling point of from 40° to 41° C. at 0.5 mbar and 429.4 g of 3-cyano-3,5,5-trimethylcyclohexanone having a boiling point of from 93° to 94° C. (0.5 mbar) are obtained. This gives a yield of 96.5% of theory, based on the hydrogen cyanide employed or 99.4% of theory, based on the isophorone reacted. The distillation residue is 7.7 g.

EXAMPLE 2

The tubular reactor described in example 1 is shortened to a length of 3 m.

A mixture of 94.43 g of isophorone and 9.23 g of hydrogen cyanide is metered hourly into the stirred reactor C1 by means of the pump P1 from the tank B1, and 1.014 g of a 15% strength solution of sodium methoxide in methanol is metered into C1 by means of the pump V2 from the tank B2. The reaction mixture continuously leaving the reactor is fed to the subsequent reactor C2 by means of the pump P3. The reactors are kept at a reaction temperature of 160° C. The HCN-free reaction mixture collected in the collecting tank B3 is stabilized by means of 0.34 g/h of an 85% strength phosphoric acid.

After an initial-cut time of 20 hours, 840.1 g of the stabilized crude product are fed to fractional distillation. After 6.9 g of low-boiling components are removed, 385.2 g of isophorone having a boiling point of from 40° to 42° C. and 437.8 g of 3-cyano-3,5,5-trimethylcyclohexanone having a boiling point of from 94° to 95° C. are removed by distillation at 1 mbar, corresponding to a yield of 97.1% of theory based on the HCN employed or 98.9% of theory based on the isophorone employed. The distillation residue is 10.1 g, i.e. 1.2% based on the crude product employed.

We claim:

1. A process for the continuous preparation of 3-cyano-3,5,5-trimethylcyclohexanone by base-catalyzed reaction of isophorone and hydrogen cyanide, which comprises carrying out the reaction in two separate reaction zones a) with essentially complete back-mixing and subsequently b) essentially without back-mixing.

2. A process as claimed in claim 1, wherein the reaction zone b) is a cylindrical reactor containing packing elements.

3. A process as claimed in claim 1, wherein the reaction zone b) is a cylindrical reactor containing fixed internals.

* * * * *